(12) United States Patent
Assmann et al.

(10) Patent No.: US 8,886,285 B2
(45) Date of Patent: Nov. 11, 2014

(54) CONTROL UNIT AND MEDICAL EXAMINATION APPARATUS

(71) Applicants: Stefan Assmann, Erlangen (DE); Björn Heismann, Erlangen (DE); Reto Merges, Erlangen (DE); Markus Schmidt, Nuremberg (DE); Sebastian Schmidt, Weisendorf (DE); Kera Westphal, Berlin (DE)

(72) Inventors: Stefan Assmann, Erlangen (DE); Björn Heismann, Erlangen (DE); Reto Merges, Erlangen (DE); Markus Schmidt, Nuremberg (DE); Sebastian Schmidt, Weisendorf (DE); Kera Westphal, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 15 days.

(21) Appl. No.: 13/660,113

(22) Filed: Oct. 25, 2012

(65) Prior Publication Data
US 2013/0109955 A1  May 2, 2013

(30) Foreign Application Priority Data
Oct. 31, 2011  (DE) .................. 10 2011 085 503

(51) Int. Cl.
*A61B 5/055* (2006.01)
*A61B 6/00* (2006.01)
*A61M 31/00* (2006.01)
*A61B 19/00* (2006.01)
*A61B 6/03* (2006.01)
*A61B 5/02* (2006.01)

(52) U.S. Cl.
CPC . *A61B 5/02* (2013.01); *A61B 19/00* (2013.01); *A61B 6/541* (2013.01); *A61B 6/00* (2013.01); *A61B 6/481* (2013.01); *A61B 6/03* (2013.01); *A61B 6/032* (2013.01); *A61B 5/055* (2013.01)
USPC .......... 600/411; 600/413; 600/428; 600/432; 604/66; 604/67

(58) Field of Classification Search
USPC .................. 600/411, 413, 428, 431, 432; 604/65–67
See application file for complete search history.

(56) References Cited

U.S. PATENT DOCUMENTS

| 6,503,203 | B1 * | 1/2003 | Rafter et al. ................. 600/458 |
| 6,673,033 | B1 * | 1/2004 | Sciulli et al. .................... 604/67 |
| 2002/0165445 | A1 | 11/2002 | Almon-Martin | |
| 2006/0215815 | A1 | 9/2006 | Rasche | |

FOREIGN PATENT DOCUMENTS

DE  102005041626 A1  3/2007

* cited by examiner

*Primary Examiner* — Michael Rozanski

(57) ABSTRACT

A control unit for an equipment arrangement is provided. The control unit includes an imaging modality, a measurement device for measuring a control variable and a controllable injection device for a regulatory substance influencing the control variable, wherein the injection rate of the injection device may be varied during a data acquisition such that a proposed value for the control variable is reached.

14 Claims, 1 Drawing Sheet

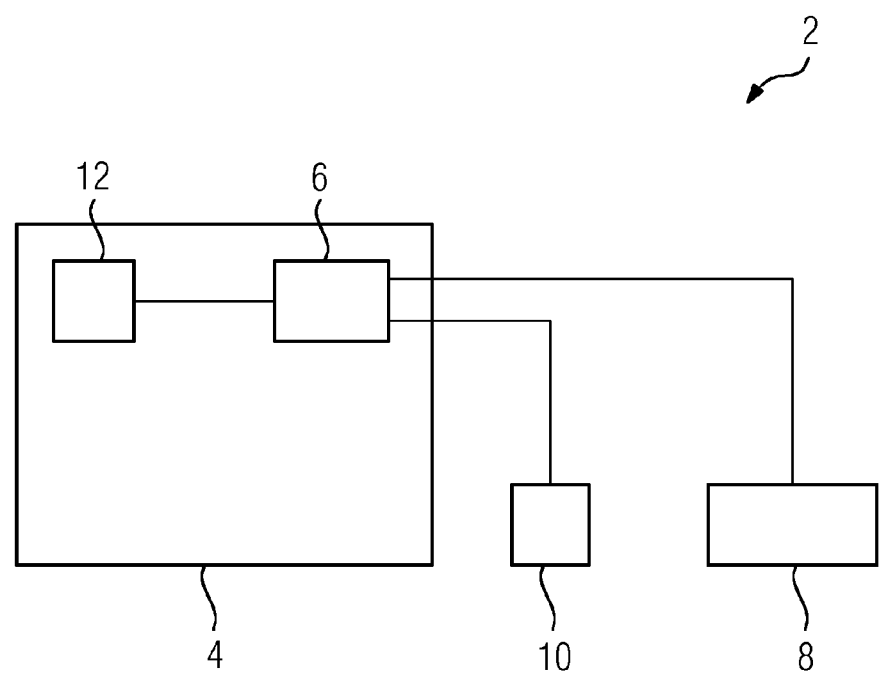

US 8,886,285 B2

CONTROL UNIT AND MEDICAL EXAMINATION APPARATUS

CROSS REFERENCE TO RELATED APPLICATIONS

This application claims priority of German application No. 10 2011 085 503.3 DE filed Oct. 31, 2011. All of the applications are incorporated by reference herein in their entirety.

FIELD OF INVENTION

A control unit and a medical examination apparatus is provided.

BACKGROUND OF INVENTION

When, for example, the cardiac perfusion, i.e. the circulation of blood through the heart, in a patient is to be examined by means of a magnetic resonance tomography (MRT) system, the cardiac perfusion is typically measured in a rest state on the one hand and in a stress state on the other. This is necessary because it can only be ascertained when coronary vessels are dilated under stress whether a stenosis, in other words a narrowing of the vessels, is functionally relevant. In the rest state the stenosis is usually "masked" by the compensatory dilation of the vessel. This means that a blood flow typical of the rest state is ensured owing to the elasticity of the vessel in spite of the narrowing. Only under stress does the blood flow rate increase to such an extent that that the narrowing possibly can no longer be compensated for by the elasticity of the vessel. Accordingly it is only revealed in the stress state whether a further opening of the vessel is possible or whether the functioning of the vessel is compromised by the narrowing to a point where it becomes problematic.

When the patient is undergoing the MRT examination, the stress state for the heart can be induced only with extreme difficulty by means of a physical stressing of the patient. Moreover, some patients are in a condition which is not conducive to their being exposed to a physical stress. For this reason the stress state for the heart is often initiated by administering a chemical substance to the patient by means of an injection.

In such a scenario it is common practice at the present time to select a dose for the patient based on the patient's body weight from a table and to inject said dose during the actual examination. The examination of the patient by means of the imaging modality, in other words the MRT system, is accordingly carried out independently of how the patient actually responds to the injection, so that the desired specification of the stress state for the purpose of investigating the cardiac perfusion is only possible to a limited extent in this case. In principle no coordination takes place between the dosage, the injection and the actual examination.

SUMMARY OF INVENTION

Starting from this premise, an object is to disclose a control unit and a medical examination apparatus with the aid of which an injection device and an imaging modality for an examination can be better coordinated with one another.

With regard to the control unit, this object is achieved by means of a control unit having the features of the claims. The related claims contain in part advantageous and in part per se inventive developments. With regard to the medical examination apparatus, this object is achieved by means of a medical examination apparatus having the features of the claims.

The control unit described herein below is provided for an equipment arrangement which comprises an imaging modality, a measurement apparatus for measuring a control variable and a controllable injection device for a regulatory substance influencing the control variable. In this arrangement the control unit is configured in such a way that the value or the development over time of at least one device parameter, in particular the injection rate, of the injection device is varied during a data acquisition such that a proposed value for the control variable is reached. A kind of closed-loop control circuit is therefore implemented by means of the equipment arrangement and used to coordinate the imaging modality, for example a magnetic resonance tomography (MRT) system or an (x-ray) computed tomography (CT) system, with the controllable injection device, for example a syringe pump, for the purpose of examining a patient. The data acquisition taking place in the course of the examination is intended to enable a medical professional subsequently to produce a diagnosis on the basis of the data generated and collected in the process.

The regulatory substance is in particular a liquid chemical substance containing a stress-initiating active agent which puts the patient's heart into a stress state, whereupon a measurement of the cardiac perfusion in the stress state is performed. Thus, in a similar manner to a so-called stress electrocardiogram (stress ECG), an examination is carried out in which the cardiovascular system, and in particular the heart, is exposed to increased stress compared to a rest state of the patient. In this case, however, the additionally imposed load or stress state for the heart is not caused by a physical stress or exertion of the patient, in other words by an additional physical activity, but as it were artificially by means of the regulatory substance and its active agent.

In this situation the measurement apparatus is used to determine the current stress level or stress state of the patient, for example by monitoring the patient's heartbeat or blood pressure. On the basis of this information the injection device is thereupon actuated such that a proposed stress level and consequently the proposed stress state is reached for example by means of a chosen injection rate for the regulatory substance and the subsequent response of the patient to the injected dosage rate of the regulatory substance. With the patient in precisely this stress state, the actual examination is then started, with image data for a later diagnosis being generated and collected as part of the data acquisition process by means of the imaging modality. The regulatory substance is not a contrast agent. However, a contrast agent is further preferably employed in addition within the scope of the actual examination of the patient by means of the imaging modality.

Through the use of the thus realized closed-loop control circuit it is possible not just to specify a proposed stress level that is particularly favorable for the chosen examination, but also to limit the stress for the patient caused by the examination and in particular by the regulatory substance to a relatively low amount. It is important to take into consideration in this situation that regulatory substances, as required for examinations in a stress state, represent a significant load for the patient's body which is associated with an altogether relevant health risk, in particular for a weakened patient. Accordingly it is desirable to choose the lowest possible dose of the regulatory substance to be administered during the examination, while at the same time it is also necessary to reach the stress level required for the examination. The majority of regulatory substances furthermore contain an active agent with which a manual dosage, based for example on a value table, tends to prove rather unfavorable and sometimes difficult, since said active agents produce very different, and therefore highly specific, reactions in potential patients. A widely used active agent is for example Adenosin®, which typically is injected at an injection rate of 2-5 ml per minute at a concentration of 3 mg per ml over a period of 5 minutes. Adenosin has a very short half-life in the region of a few seconds in the body of the patient. The half-life, which constitutes a measure of how long the patient's response to the active agent persists, is dependent in this case on the degradation rate of the active agent in the body of the patient and varies considerably from patient to patient. Accordingly, a manual dosage, in particular on the basis of a value table which specifies a dosage as a function of the patient's body weight, is extremely imprecise. By means of the herein-described control of the injection rate with simultaneous monitoring of the patient's response to the injection and a subsequent corrective regulation of the injection rate it is, in contrast, possible to successfully pursue the objective of choosing the lowest possible dose of the regulatory substance to be administered and at the same time produce the proposed stress condition.

In this situation the injection rate is not, however, in all cases the only device parameter whose value or whose variation with time is predefined and preferably varied automatically by the control unit in order to reach the proposed value for the control variable. Depending on the embodiment of the control unit, further device parameters, such as for example the temperature of the regulatory substance or a mixing ratio between a regulatory substance concentrate and a solvent, are provided in addition or alternatively.

Also of advantage is a variant of the control unit in which the equipment arrangement includes a monitoring device which is used for measuring a check variable which can be influenced by the regulatory substance. In this case the monitoring device serves in particular as an additional safeguard for the patient. It is used to check whether the patient's response to the injected regulatory substance follows the predicted course or whether for example an unexpected or undesirable response occurs due to an allergic reaction. Depending on its embodiment, the monitoring device is in this case realized by means of the measurement device as well as the control unit, though a variant is preferred in which an additional and preferably independently operating monitoring device is used for monitoring the check variable. If an abnormal, i.e. undesirable, trend in the development over time of the check variable is indicated or if the latter deviates from a reference value, the equipment arrangement, and in particular the injection device, is switched to a safety mode of operation. In the case of the examination of the cardiac perfusion by means of MRT provision is for example made to use the measurement device to measure the blood pressure as a control variable and at the same time to monitor the patient's heartbeat as a check variable by means of the monitoring device. By adjusting the injection rate for the regulatory substance, the patient's blood pressure is raised to a predefined value for the actual examination. The patient's heartbeat is monitored in parallel in order to ensure that the patient is not subjected to any problematic stress over the course of the entire examination. If the check variable monitored by means of the monitoring device, in this case, by way of example, the patient's heartbeat, exceeds a predefined threshold or limit value, an alarm event is triggered by the monitoring device, for example in that an audible or visual signal is output.

In an advantageous development, an alarm event leads to the equipment arrangement being switched to a safety mode. In this case, depending on the particular embodiment variant, the transition to the safety mode is initiated by the monitoring device itself or by the control unit, which in this case either is actuated by the monitoring device or accesses the monitoring device's information by way of a signal communication connection. Since by preference the equipment arrangement is switched to a safety mode fully automatically, a time delay, due for example to an operator's reaction time, can be avoided, as a result of which critical situations for the patient can be ruled out to the maximum possible extent.

Beneficial in this regard is an embodiment of the control unit in which the injection rate of the injection device is reduced in the safety mode. As a result the patient's stress state is usually also reduced to a lower level if an alarm event occurs, thereby avoiding a possible critical situation for the patient. Even if in this case the initially proposed value for the control variable is not reached, there is still the possibility that the stress level reached at this point in time is sufficient for the actual examination to such an extent that the already running examination does not have to be aborted without a data acquisition.

Alternatively hereto it is provided to switch off the injection device in the safety mode. In this case the injection, and preferably also the entire examination, is instantly aborted irrespective of whether the data acquisition has been completed or could still be completed. Such an immediate termination of the injection of the regulatory substance is provided in particular for regulatory substances which produce an especially strong effect in the patient and in which for that reason a reduction in the injection rate does not result in a sufficiently rapid reversal of the stress level.

According to a further advantageous embodiment of the control unit, a first and a second limit value are specified for the check variable, the injection rate of the injection device being reduced if the check variable exceeds the first limit value, and the injection device being switched off if the check variable exceeds the second limit value. In this way a two-stage safety system is realized in which the advantages of the two above-described variants are combined. After the first limit value has been reached there is initially effectively a waiting interval to establish whether or not the desired lowering of the stress level is achieved by means of a predefined reduction in the injection rate or by means of a multiple, in particular stepwise, reduction in the injection rate. Only when the reaching of the second limit value thereupon indicates that the desired reduction in the stress level cannot be achieved, or cannot be achieved sufficiently rapidly, by a reduction in the injection rate, is the injection aborted completely.

It is furthermore of advantage if the injection rate is increased during the data acquisition, starting from a predefined base value, at a predefined rate of increase until the proposed stress state is reached. In this way the injection rate which brings about the proposed stress state in the individual patient is approached incrementally with each examination.

A contrast agent is expediently injected in addition to the regulatory substance, a common injection device preferably being used for this purpose.

According to another very beneficial embodiment variant, the measurement device and/or the monitoring device are/is embodied for measuring a heart rate, the heart rate being provided as a control variable and/or as a check variable. The heart rate is suitable for example during the cardiac perfusion examination both as a control variable which represents the stress state of the heart, and as a check variable which accurately reflects the general condition of the patient. For this specific examination it is accordingly possible to realize a particularly simple equipment arrangement in which the measurement device and the monitoring device are embodied by means of a common device. It is, however, preferred that the measurement device and the monitoring device are realized by means of redundantly operating measurement devices which are preferably controlled by a common control unit. In addition, a further alternative embodiment is provided in which the measurement device and the monitoring device are in each case realized by means of an independent device including a dedicated control unit, and in which the control units are connected to one another for signal communication purposes, in which case the control unit of the monitoring device takes precedence over the control unit of the measurement device if an alarm event occurs.

Suitable in particular for directly or indirectly determining the heart rate are what is known as a trigger ECG, which is provided as standard in any case in a variety of imaging modalities, such as for example in a computed tomography system, a pulse oxymeter preferably integrated into the imaging modality, an acoustic measuring instrument, an optical measuring instrument, which records and analyzes the movements of the patient's thorax, a radar device, or the imaging modality itself, wherein in this case for example the changes in the magnetic resonance signal of the coils, the image data or the so-called k-space data are evaluated and analyzed.

If the heart rate is provided as a control variable and/or as a check variable, then the proposed stress state is also defined or specified by way of precisely said heart rate, a value greater for example than 100 beats per minute being provided. Alternatively or in addition, the proposed stress state can be defined by way of a deviation with respect to a rest state, the heart rate in the proposed stress state being increased for example by at least 20 beats per minute compared to the rest state.

In addition to the heart rate, the patient's blood pressure is also suitable for being used both as a control variable and as a check variable. Accordingly, an implementation of the control unit is provided in which the measurement device and/or the monitoring device are/is embodied for measuring the blood pressure.

A variant of the control unit is furthermore provided in which the measurement device and/or the monitoring device are/is embodied for measuring a blood flow, the blood flow in this case being provided as a control variable and/or as a check variable. Not only the heart rate but also the blood pressure and the blood flow have proved particularly suitable variables for regulatory and/or for monitoring purposes.

An embodiment variant of the control unit is beneficial in which the measurement device and/or the monitoring device are/is embodied for measuring and evaluating a heart rate or a heartbeat rhythm, and in which the measurement device and/or the monitoring device derive/derives the control variable and/or the check variable from the heart rate or the heartbeat rhythm respectively. Preferably, in the process, not only is a heart rhythm measured, but in addition the sum total of all electrical activities of all the cardiac muscle fibers is recorded for example by means of an electrocardiogram device, ECG device for short. In this case the control variable or the check variable is then determined not just on the basis of a change in the heart rhythm, but on the basis of all changes in the electrical activities of the cardiac muscle fibers. For example, it is provided to examine the recorded electrocardiogram for extra systoles or other rhythm disturbances, for example what are called irregular R-R intervals, and in the event of corresponding deviations from the normal curve of the electrocardiogram to reduce the injection rate for the regulatory substance on the injection device or to abort the injection completely. It is particularly advantageous in this case to use the aforementioned trigger ECG, which is provided as standard in any case in different imaging modalities. With a minor modification, i.e. an adaptation of the software for example, such a trigger ECG can additionally be used as a measurement device and/or as a monitoring device.

Also of advantage is a variant of the control unit in which the measurement device and/or the monitoring device are/is embodied for evaluating the image data generated by means of the imaging modality and in which the measurement device and/or the monitoring device derive/derives the control variable and/or the check variable from the generated image data. For example, the cardiac function and in particular the movement of the cardiac walls can be measured with the aid of instruments and from this in turn can be determined the value for what is called the myocardial thickening, which is suitable both as a control variable and as a check variable.

According to a particularly beneficial embodiment of the examination device, a central control unit of the imaging modality is provided as the control unit. In this case the central control unit of the imaging modality takes over the additional tasks which alternatively are fulfilled by an independent control unit. Since an imaging modality frequently possesses a central control unit as standard in any case, the safety concept presented here can in this way be realized effectively by retrofitting at relatively low cost even in medical examination apparatuses which are already in use. In the most favorable case it is then simply necessary to implement changes in the area of the data exchange between the individual devices of the examination apparatus as well as modifications to the control software of the individual components.

In the interest of particularly good compatibility it is furthermore provided in a variant of the examination apparatus to use standardized connections, such as e.g. "CAN bus" or "Bluetooth", and standard protocols for communication between the control unit, the imaging modality and the controllable injection device.

Also beneficial is a control unit variant in which the measurement device and/or the monitoring device are/is integrated into the imaging modality, as is so for example in the above-described case of the trigger ECG, which is typically part of the corresponding computed tomography system. In such an integrated implementation the components, which are in most cases embodied in module-like fashion, i.e. in this instance the computed tomography system and the trigger ECG, are particularly well matched to one another.

An embodiment of the control unit is furthermore provided in which a limit value is specified for the injection rate and/or for the total dosage of the regulatory substance, the control unit preventing, preferably fully automatically, said limit value from being exceeded by means of a corresponding actuation of the injection device. In this case the corresponding limit value is preferably specified at a preliminary stage of the examination and is adjusted to the individual patient as well as to the respective examination. As an example, a limit value of approximately 5 ml per minute is expedient for the injection rate.

Also provided is an embodiment of the control unit having an additional safety function in which the alarm event is triggered if the control variable undergoes no relevant change within a predefined waiting time of for example 3 minutes. In this case an incorrect injection of the regulatory substance could be present, for example, for which reason the equipment arrangement and in particular the injection device are, in the case of the alarm event too, preferably switched to the safety mode.

BRIEF DESCRIPTION OF THE DRAWINGS

More detail is provided below with reference to a schematic drawing, in which:

FIGURE shows a medical examination apparatus represented in a block diagram.

DETAILED DESCRIPTION OF INVENTION

In the case of the medical examination apparatus 2 described hereinbelow and represented schematically in FIGURE, a magnetic resonance tomography system 4, MRT 4 for short, having a central control unit 6 is used for examining a patient by means of an imaging method. Depending on the chosen examination method, it is additionally provided to inject a regulatory substance into the patient. For this purpose the medical examination apparatus 2 includes an injection device 8, embodied in this instance by way of example as a syringe pump, also known as a dosing pump.

The injection device 8 used in the exemplary embodiment is a controllable injection device 8 which is connected to the control unit 6 of the MRT 4 for signal communication purposes and which is actuated by way of the control unit 6. In this way the injection of the regulatory substance and in particular the variation with time of the injection rate of the regulatory substance are adjusted to the chosen examination and to the individual patient in order by this means to exert a positive influence on the quality and the relevance of the image data that is to be generated.

Prior to the commencement of a corresponding examination the patient is positioned on an examination table of the MRT 4. In addition, assuming an injection of the regulatory substance is provided as in this case, an injection needle, which is part of the injection device 8, is introduced into the patient's body, typically into a vein. An operator, that is to say e.g. a medical technical assistant (MTA), then selects a control program for the control unit 6 by way of a console (not shown in more detail), by entering a set of parameters for example, the control program specifying how the MRT 4 on the one hand and the injection device 8 on the other are subsequently to be controlled during the examination.

The medical examination apparatus 2 also includes an ECG device for determining and recording the electrical activities of the cardiac muscle fibers of the patient, as well as an evaluation unit 12 which, as part of the MRT 4, analyzes and evaluates generated image data.

In the case of a proposed cardiac perfusion examination, i.e. an investigation of the blood circulation through the patient's heart, as described hereinbelow by way of example, by means of the MRT 4, the blood circulation through the heart or cardiac perfusion are measured in what is termed a stress state. For this purpose the patient is injected with the regulatory substance by means of the injection device 8, whereupon the patient's heartbeat, blood pressure and blood flow increase. In order to ensure that a medical professional can assess the condition of the patient as accurately as possible and reach a diagnosis, in this case a problematic stenosis for example, on the basis of the image data generated over the course of the examination, it is advantageous to carry out the actual examination in which the image data is generated in a predefined stress state, i.e. at a predefined stress level of the patient. It is important to be aware in this case that for the patient the administered regulatory substance represents a stress which is undesirable per se and which on the one hand is necessary for the purpose of the examination and on the other hand should be kept to as low a level as possible.

For this reason the desired stress state is induced under very close control and the proposed stress level is set with a maximum degree of precision. Toward that end a start value for the injection rate of the regulatory substance is first set by way of the control unit 6 on the injection device 8, said start value having been selected from a value table as a function of the patient's body weight. The injection rate is subsequently increased gradually, for example initially by 0.5 ml per min$^2$, until the proposed stress level, which in this case is given by a specific value for the blood flow, is reached.

In parallel, the blood flow through the patient's heart is determined by means of the MRT 4 and the evaluation unit 12 and supplied to the control unit 6 as a control variable. As a function of the value of the control variable the control unit 6 thereupon varies the injection rate for the regulatory substance on the one hand and the change in the injection rate per time interval on the other hand on the controllable injection device 8 until the predefined value for the blood flow is established. Accordingly, the MRT 4 together with the evaluation unit 12, the control unit 6 and the injection device 10 embody a closed-loop control circuit with the aid of which precisely the amount of regulatory substance is supplied to the patient which is necessary to induce the desired stress level and consequently the desired stress state in the patient. An expedient stress state is given for example when the blood flow lies 20% above the value in the rest state.

Because the patient is subject to stress due to the regulatory substance and the administration of the regulatory substance therefore represents a risk to the patient, the patient's response to the regulatory substance is monitored in addition by means of a monitoring device, which is realized by means of the ECG device 10 and the control unit 6, in order to assure the patient's safety. This entails using measurement techniques to measure the patient's heartbeat and in particular the heartbeat rate by means of the ECG device 10. If the heart rate exceeds a first limit value, for example 120 heartbeats per minute, the control unit 6 disables the regulation of the injection rate for the regulatory substance by means of the closed-loop control circuit and reduces the injection rate in stages according to a stored value table until the heart rate has decreased again to the first limit value. If no lowering of the heart rate is achieved as a result of reducing the injection rate and if the heart rate exceeds a second limit value, for example 160 beats per minute, then the control unit 6 stops the further injection of the regulatory substance altogether. An additional safeguard of this kind reduces the risk of an excessive stress being applied and hence of a critical situation for the patient. It is important to take into consideration in this case that in addition to the intended effect of the regulatory substance undesirable side-effects may also occur, such as allergic reactions for example.

In order to determine the blood flow with the aid of the MRT 4 and the evaluation unit 12 use is preferably made of measurement methods which are already available in magnetic resonance tomography systems which are currently deployed, i.e. arterial spin labeling (ASL) or flow-sensitive sequences for example.

As a further safeguard for the medical examination apparatus 2 to prevent a deficient examination it is furthermore provided to abort the injection of the regulatory substance and preferably the entire examination if no change in the control variable, i.e. in the blood flow in the case described by way of example here, is registered by means of the imaging modality, i.e. the MRT 4 together with the evaluation unit 12, after a predefined waiting time, for example 3 minutes, has expired.

We claim:

1. A control unit for a medical examination apparatus, comprising:
   an imaging modality for acquiring image data of a patient;

a controllable injection device for injecting a regulatory substance into the patient to reach a proposed stress sate of the patient in order to acquire the image data of the patient; and a measurement device for measuring a control variable of the patient that is influenced by the regulatory substance, wherein the control unit is configured to:
- set a limit value of the control variable,
- set a start value of an injection rate of the injection device for injection the regulatory substance into the patient based on body weight of the patient,
- subsequently increase the injection rate of the injection device at a predefined rate until the proposed stress state of the patient is reached incrementally during the data acquisition, and
- adjust the injection rate of the injection device based on the control variable of the patient to safely reach the proposed stress state of the patient during the data acquisition, and
- trigger an alarm if the control variable exceeds the limit value.

2. The control unit as claimed in claim 1, wherein the medical examination apparatus is switched to a safety mode when the alarm is triggered.

3. The control unit as claimed in claim 2, wherein the injection rate of the injection device is decreased in the safety mode.

4. The control unit as claimed in claim 2, wherein the injection device is switched off in the safety mode.

5. The control unit as claimed in claim 1,
wherein a first and a second limit value are specified for the control variable,
wherein the injection rate of the injection device is reduced when the control variable exceeds the first limit value, and
wherein the injection device is switched off when the control variable exceeds the second limit value.

6. The control unit as claimed in claim 1, wherein a contrast agent is injected in addition to the regulatory substance.

7. The control unit as claimed in claim 1,
wherein the measurement device is embodied for measuring a heart rate of the patient, and
wherein the heart rate is provided as the control variable.

8. The control unit as claimed in claim 7,
wherein the proposed stress state is established at a heart rate greater than 100 beats per minute.

9. The control unit as claimed in claim 7, wherein the heart rate in the proposed stress state is increased by at least 20 beats per minute compared to a rest state.

10. The control unit as claimed in claim 1,
wherein the measurement device is embodied for measuring a blood pressure of the patient, and
wherein the blood pressure is provided as the control variable.

11. The control unit as claimed in claim 1,
wherein the measurement device is embodied for measuring a blood flow of the patient, and
wherein the blood flow is provided as the control variable.

12. The control unit as claimed in claim 1,
wherein the measurement device is embodied for measuring a heartbeat rhythm, and
wherein the heartbeat rhythm is provided as the control variable.

13. The control unit as claimed in claim 1,
wherein the measurement device is embodied for evaluating the acquired image data, and
wherein the evaluated image data is provided as the control variable.

14. A medical examination apparatus, comprising:
a control unit as claimed in claim 1.

* * * * *